(12) United States Patent
Sablone

(10) Patent No.: US 9,364,373 B2
(45) Date of Patent: Jun. 14, 2016

(54) METHOD FOR PRODUCING SANITARY ARTICLES WEARABLE AS PANTS PROVIDED WITH SIDE PANELS

(71) Applicant: Fameccanica.Data S.p.A., Pescara (IT)

(72) Inventor: Gabriele Sablone, Montesilvano (IT)

(73) Assignee: Fameccanica Data S.P.A., Pescara (IT)

(*) Notice: Subject to any disclaimer, the term of this patent is extended or adjusted under 35 U.S.C. 154(b) by 30 days.

(21) Appl. No.: 14/553,001

(22) Filed: Nov. 25, 2014

(65) Prior Publication Data
US 2015/0202091 A1    Jul. 23, 2015

(30) Foreign Application Priority Data
Jan. 21, 2014  (IT) ............... TO2014A0034

(51) Int. Cl.
| | |
|---|---|
| *B32B 37/00* | (2006.01) |
| *A61F 13/15* | (2006.01) |
| *A61F 13/56* | (2006.01) |
| *B32B 37/06* | (2006.01) |
| *B32B 37/10* | (2006.01) |
| *B32B 37/18* | (2006.01) |

(52) U.S. Cl.
CPC ..... *A61F 13/15585* (2013.01); *A61F 13/15699* (2013.01); *A61F 13/15747* (2013.01); *A61F 13/15756* (2013.01); *A61F 13/5633* (2013.01); *B32B 37/0076* (2013.01); *B32B 37/06* (2013.01); *B32B 37/10* (2013.01); *B32B 37/18* (2013.01); *A61F 2013/15878* (2013.01); *B32B 2310/028* (2013.01); *B32B 2555/02* (2013.01); *Y10T 156/10* (2015.01)

(58) Field of Classification Search
CPC ............ A61F 13/15585; A61F 13/15699; A61F 13/15747; A61F 13/15756; A61F 13/15804; B32B 37/18; B32B 37/0076; B29C 65/7832; B29C 65/7855; B29C 66/1122; B29C 66/43
USPC ............. 156/204, 226, 227; 604/385.04
See application file for complete search history.

(56) References Cited

U.S. PATENT DOCUMENTS

| | | | |
|---|---|---|---|
| 8,440,039 B2 * | 5/2013 | Nakakado | A61F 13/15747 156/204 |
| 2011/0100536 A1 | 5/2011 | Umebayashi | |

FOREIGN PATENT DOCUMENTS

| | | |
|---|---|---|
| EP | 0295957 A1 | 12/1988 |
| EP | 1941853 A1 | 7/2008 |

(Continued)

OTHER PUBLICATIONS

Italian Search Report and Written Opinion dated Sep. 2, 2014 for Application No. TO2014A000034.

*Primary Examiner* — John Goff
(74) *Attorney, Agent, or Firm* — Patterson & Sheridan, LLP

(57) ABSTRACT

A method for producing sanitary articles wearable in the manner of pants, provided with at least one pair of side panels suitable for connecting the end parts of the article around the user's waist, and with a topsheet produced by assembling together a central web, permeable to body fluids and a first and a second side material. The production method comprises the steps of partially overlapping the first end regions of the side panels, leaving the second end regions uncovered, and then joining in a provisional manner, the parts of the overlapping side panels in order to produce a temporary laminate on which it is possible to identify a first surface and a second surface.

9 Claims, 5 Drawing Sheets

(56) References Cited

FOREIGN PATENT DOCUMENTS

| IT | WO 2012131509 A1 | * | 10/2012 | ........ A61F 13/15756 |
| WO | 01/91666 A2 | | 12/2001 | |
| WO | 01/92013 A1 | | 12/2001 | |
| WO | 2011101773 | | 8/2011 | |

* cited by examiner

METHOD FOR PRODUCING SANITARY ARTICLES WEARABLE AS PANTS PROVIDED WITH SIDE PANELS

CROSS-REFERENCE TO RELATED APPLICATIONS

This application claims benefit of Italian patent application number TO2014A000034, filed Jan. 21, 2014, which is herein incorporated by reference.

BACKGROUND OF THE INVENTION

1. Field of the Invention

The present description relates in general to the production of sanitary articles of the type wearable as pants.

2. Description of Prior Art

In particular, the description relates to the production of sanitary articles comprising a central body to which a pair of side panels is connected, at least at one end.

The designation of sanitary articles is used here in its broadest sense, to include, for example, diapers for babies and incontinence products.

In the field of sanitary articles wearable as pants (diapers for children and infants, incontinence pads, etc.) a sanitary article has become widespread that has at least one pair of panels, provided with appropriate closing/coupling elements, applied to the side edges of the absorbent product at one of its end regions.

Documents such as, for example, EP-A-1 941 853 describe methods for producing sanitary articles wearable as pants with a structure with side panels, said absorbent products comprise:

a central body that extends in the longitudinal direction between two opposite ends, capable of being placed around the groin region (crotch portion) of the user, and at least one pair of side panels, connected to one end of said central body and able to define, at least in part, the waist-line of the article.

Typically, such sanitary articles are absorbent products that comprise an absorbent element (core) arranged in the central body.

The solution described in EP-A-1 941 853 involves producing side panels, by segmenting a respective tape element with cutting operations, at least partly produced in an oblique direction with respect to the general direction of extension of said respective tape element, and to impart to one panel in two, in an alternating sequence, a movement of 180° rotation/overturning, before the application of the panels to the central body. After this rotation/overturning movement, all the panels are correctly oriented to be applied to the central body of the article.

The solution described in EP-A-1 941 853 proves to be entirely satisfactory for producing sanitary articles intended for infants and children.

However, the described solution can be further improved to be able to manage the manufacturing processes more effectively, in particular of applying and folding large-sized side panels especially present in products intended for incontinent adults.

In these cases, articles of significant size are considered: for example, a length of about one meter and a total width of about 90 cm, in order to reach circumferences of the finished article of up to the order of 180 cm where, precisely, the production operations, in particular folding, of the side panels can be very critical to implement in the presence of articles of these dimensions, also considering the very high production rates (hundreds of articles per minute) that are required. In any case, the need is perceived, independently of the size of the article, to produce absorbent articles with structures of this type with more efficient equipment and manufacturing processes and therefore cheaper than the traditional production systems.

SUMMARY OF THE INVENTION

The prior art to which reference is made leaves room for improvement on two fundamental problems: the first, is that of providing side panels for sanitary articles that can be made without wasting material and which lend themselves to be equipped with protruding closing elements such as, for example, adhesive labels or provided with mechanical coupling systems; the second, is that of applying said side panels onto individual absorbent products with a simple and economic method, i.e. of easy management and operation that eliminates successive processing operations of the side panels themselves.

According to the present invention, this object is achieved thanks to a method having the characteristics referred to in claim 1. Advantageous developments of the invention form the subject of the dependent claims. The invention also relates to a corresponding sanitary article produced with the present method.

The claims form an integral part of the technical disclosure provided here in relation to the invention.

BRIEF DESCRIPTION OF THE DRAWINGS

The invention will now be described, purely by way of non-limiting example, with reference to the attached figures, in which.

DETAILED DESCRIPTION

In the following description various specific details are illustrated, aimed at a thorough understanding of the embodiments. The embodiments can be implemented without one or more of the specific details, or with other methods, material components, etc. In other cases, known structures, materials or operations are not shown or described in detail, to avoid obscuring the various aspects of the embodiments.

The reference to "an embodiment" in the context of this description indicates that a particular configuration, structure or characteristic described in relation to the embodiment is included in at least one embodiment. Therefore, phrases such as "in an embodiment", possibly present in different places of this description do not necessarily refer to the same embodiment. Furthermore, particular conformations, structures, or characteristics can be combined in any suitable manner in one or more embodiments.

The references used herein are for convenience only and therefore do not define the field of protection or the scope of the embodiments.

Figure 1:
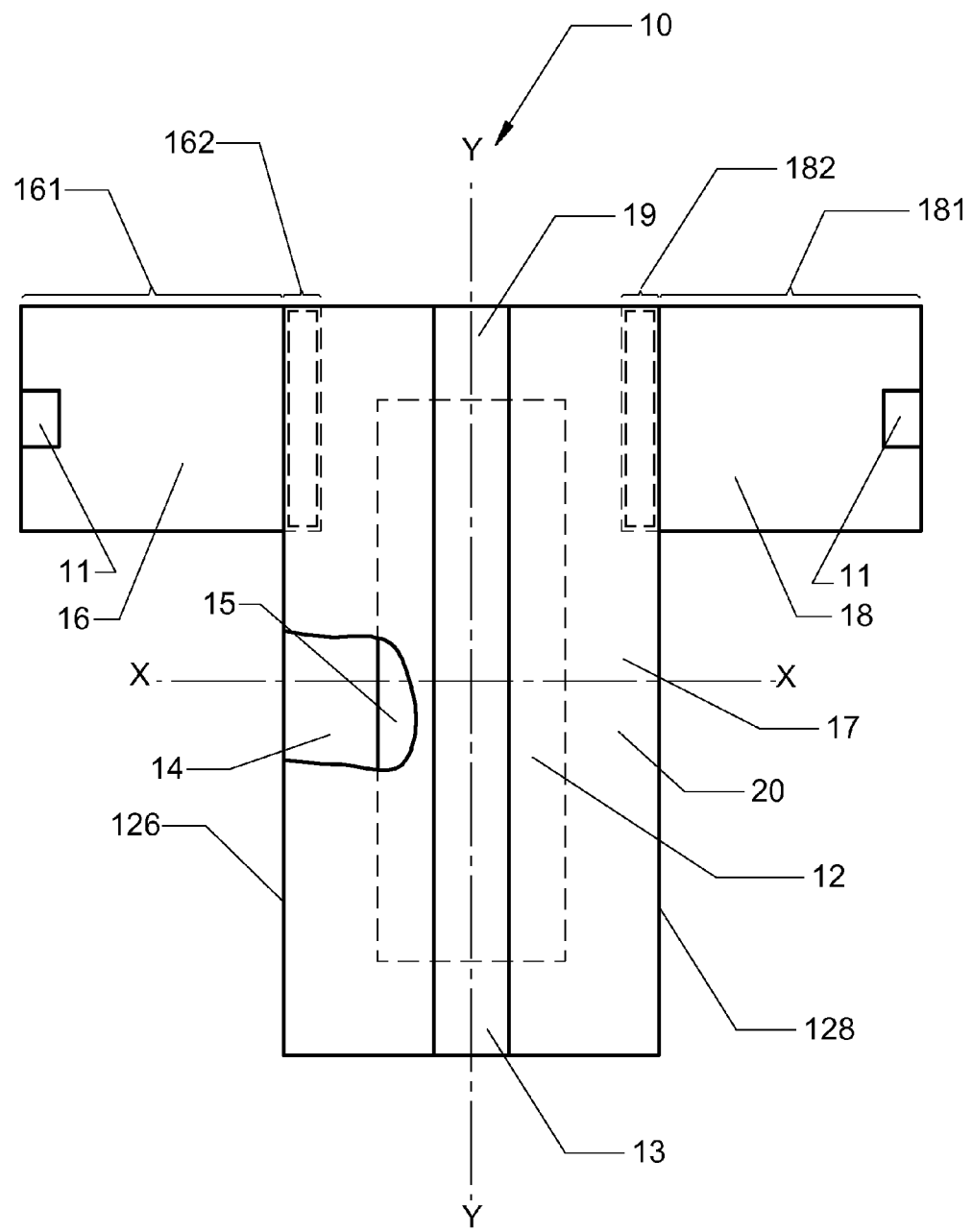
FIG. 1 is a general plan view of a sanitary article wearable as pants provided with side panels, of the type described herein, represented in the extended position.

In FIG. 1, the numeric reference 10 indicates, in its entirety, a sanitary product of the conventional type, wearable as pants, intended to be sold open and to be closed only after being positioned on the user's body.

The absorbent sanitary product 10 comprises a central structure 12, intended to be applied around the groin area (crotch portion) of the user, according to a general U- or basin-shaped conformation.

Typically, the central structure (or chassis) 12 has a configuration in which the following are recognizable:
  a topsheet 20 intended to be facing towards the user's body;
  a backsheet 14, impermeable to body fluids, intended to be facing outwards, i.e. in contact with the clothing worn by the user; and
  an absorbent core 15, interposed between the topsheet 20 and the backsheet 14.

The central structure or chassis 12 comprises: a first waist region 19, a second waist region 13, and a crotch region 17, interposed between the two waist regions 19, 13.

On the central structure, it is also possible to identify a first side edge 126, and a second side edge 128, as well as a longitudinal axis Y-Y and a transverse axis X-X, perpendicular to each other.

In the preferred embodiment of FIG. 1, the first waist region 19 is provided with a pair of side panels formed by a first side panel 16 and a second side panel 18, which extend outwardly from the respective first and second side edges 126 and 128 of the central body 12. Each side panel 16, 18 has, respectively, a first end region (or distal) 161, 181, which is typically the part of the panel that projects externally to the central body 12, and a second end region (or proximal) 162, 182, which is the part of the panel that connects to the main body 12.

The side panels 16 and 18, at the first end regions 161 and 181, can be provided with coupling systems 11 of the type with micro hooks or adhesives that enable closing of the absorbent sanitary article around the waist of the user, in order to give it the classical pants-configuration.

In the preferred embodiment described below, the topsheet 20 is a sheet material produced by assembling together three distinct sheets of material, among which the following are recognizable: a central web 21, permeable to body fluids and a first and a second side sheet (or material) 22 and 24.

Figure 3:
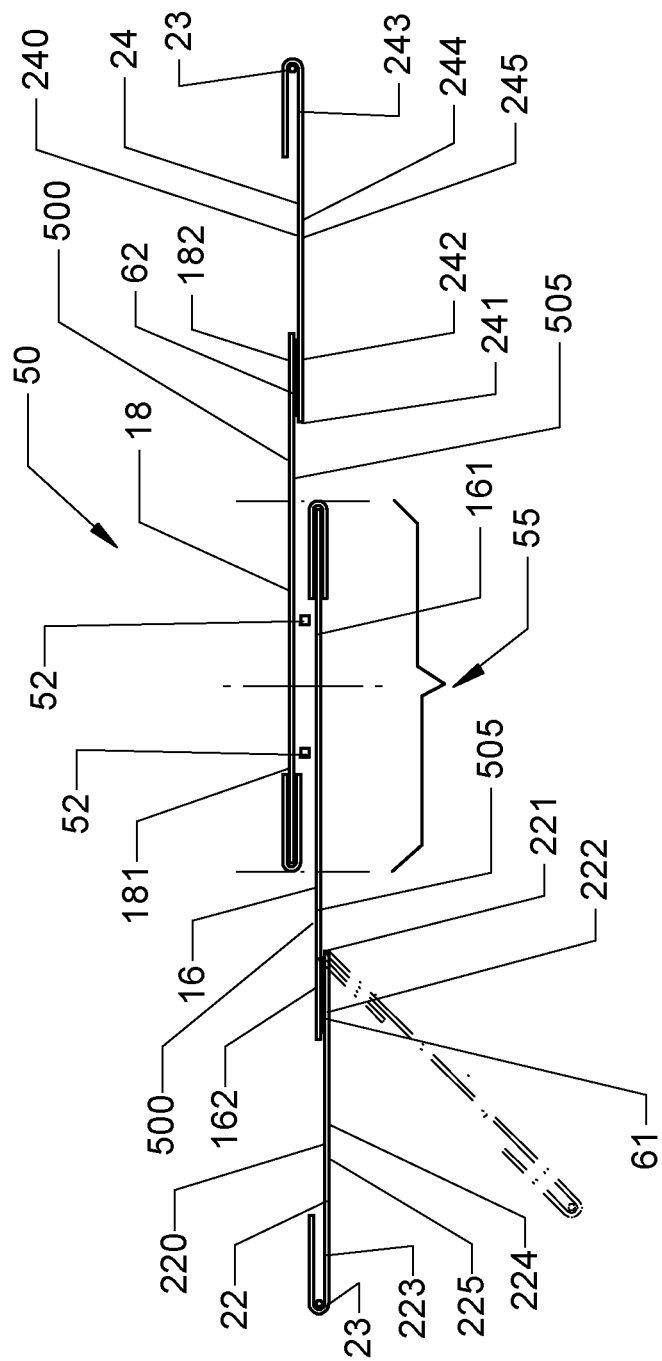
FIG. 3 is a cross-sectional view according to the line III-III of FIG. 2.
Figure 5:
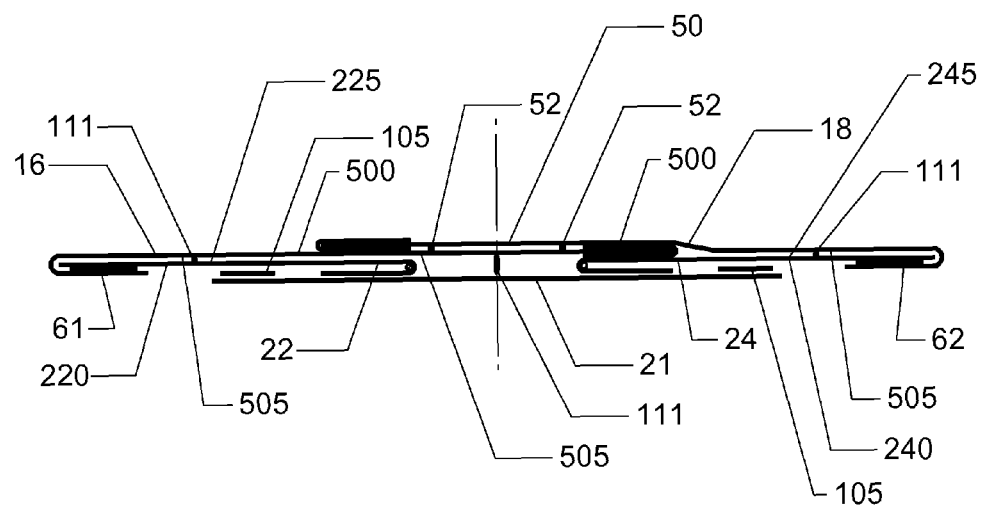
FIG. 5 is a cross-sectional view along the line V-V of FIG. 2.

As clearly illustrated in FIGS. 3 and 5, on each of the aforesaid side materials 22, 24, it is possible to identify a first end edge 221, 241, a first end region 222, 242 adjacent to the respective end edge 221, 241, a second end region 223, 243, an intermediate region 224, 244 between the end regions of the respective side material, a first surface 220, 240 and a second surface 225, 245 (FIG. 3).

To improve the effect of liquid containment, the end regions 223 and 243 of the side sheets 22 and 24 can be provided with elastic elements 23 which, in the moment in which the absorbent product 10 is shaped with a basin-conformation in order to be worn, they contribute to raising the aforesaid second end regions 223 and 243 of the side materials 22 and 24.

The materials for producing the sheets necessary for constructing the topsheet 20 can be chosen from natural fibers or synthetic ones, such as polyester or polypropylene, or a mixture of synthetic and natural fibers may be used. A suitable material for producing the liquid-permeable central web 21 of the topsheet 20 is a nonwoven material of 25 g/m$^2$ polypropylene fibers, produced by Spunbond technology, rendered hydrophilic through a surface treatment with surfactant products such as Ahcovel N-62 by Hodgson Textile Chemicals of Mount Holly, N.C. U.S.A. and/or Glucopan 220UP by the Henkel Corporation of Amber, Pa. U.S.A.

The tapes or side materials 22 and 24 can be produced by various methods, structures and materials. In the patent literature, several examples of side tapes or cuffs, suitable for our purpose, are available; purely by way of example see EP-A-0263720 "Absorbent article having leakage resistant dual cuffs".

The side panels 16 and 18 can be produced with materials manufactured according to the criteria better described in the documents WO-A-01/91666 and WO-A-01/92013. This also refers to the possibility of giving "breathability" characteristics to the panels 16 and 18, with the formation of openings that allow the passage of vapor, and contribute to keeping the user's skin dry.

In further embodiments, the side panels may be present in both the waist regions 13 and 19 of the central body 12, giving the absorbent article 10 an hourglass conformation.

Figure 2:
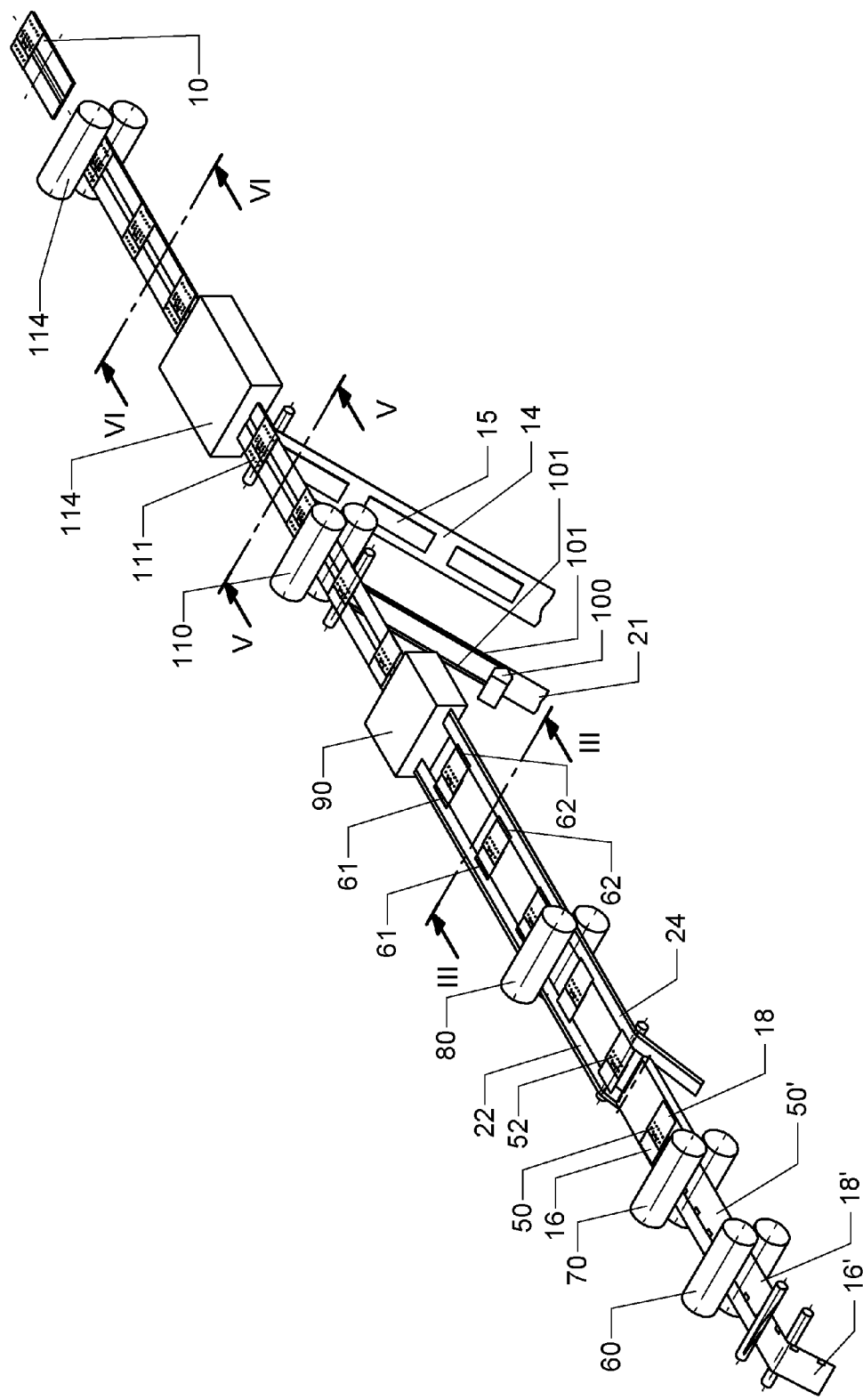
FIG. 2 is a general perspective view of a system usable for producing and applying the side panels, operating according to one embodiment.

In FIG. 2, a manufacturing method 40 is schematically shown, capable of producing sanitary articles 10 according to a preferred embodiment of the present invention.

The method 40 comprises the steps of partially overlapping the side panels 16 and 18, intended to be applied on the same sanitary article, so that the first end region 161 of the first side panel 16, and the first end region 181 of the second side panel 18 (as shown in greater detail in FIG. 3), are in contact with each other in an overlapping area 55 and so that the second end region 162 of the first side panel 16, and the second end region 182 of the second side panel 18 remain uncovered.

Once they are overlapping, the two side panels 16, 18 are joined together with small amounts of glue or with provisional welding points, in order to form a temporary laminate 50, which has the characteristic of being able to be separated again into the original elements that form it, without damaging them and without having to apply excessive force. Temporary unions with these characteristics are well known and are called "technical welds".

On the temporary laminate 50 it is, furthermore, possible to identify a first surface 500 and a second surface 505, clearly illustrated in FIG. 3.

A reliable method for producing a provisional laminate 50, as described above, is well represented in the preferred embodiment of FIG. 3, where the side panels 16 and 18 partially overlap with each other when they are still in the form of continuous tapes 16' and 18', then they are passed through a welding unit 60, which envisages the production of a plurality of provisional thermo-mechanical welds 52 obtaining, therefore, a continuous provisionally-welded tape 50'.

In the preferred embodiment, illustrated in FIG. 2, once the provisional laminate 50' is produced, it is passed through a cutting unit 70, which envisages its segmenting in order to produce a plurality of provisional laminates 50, which are subsequently spaced apart, and then joined to the two side tapes 22 and 24 with the respective joints 61 and 62 shown in greater detail in FIGS. 3 and 4.

Specifically, and referring to the constituent elements of each provisional laminate 50, the second end regions 162 and 182 of the first side panel 16 and the second side panel 18, respectively, are joined to the first end regions 222 and 242 of each side material 22 and 24; in this way, a first and a second overlapping region 64 and 65 are typically formed, on which the joints 61 and 62 are produced.

Figure 4:
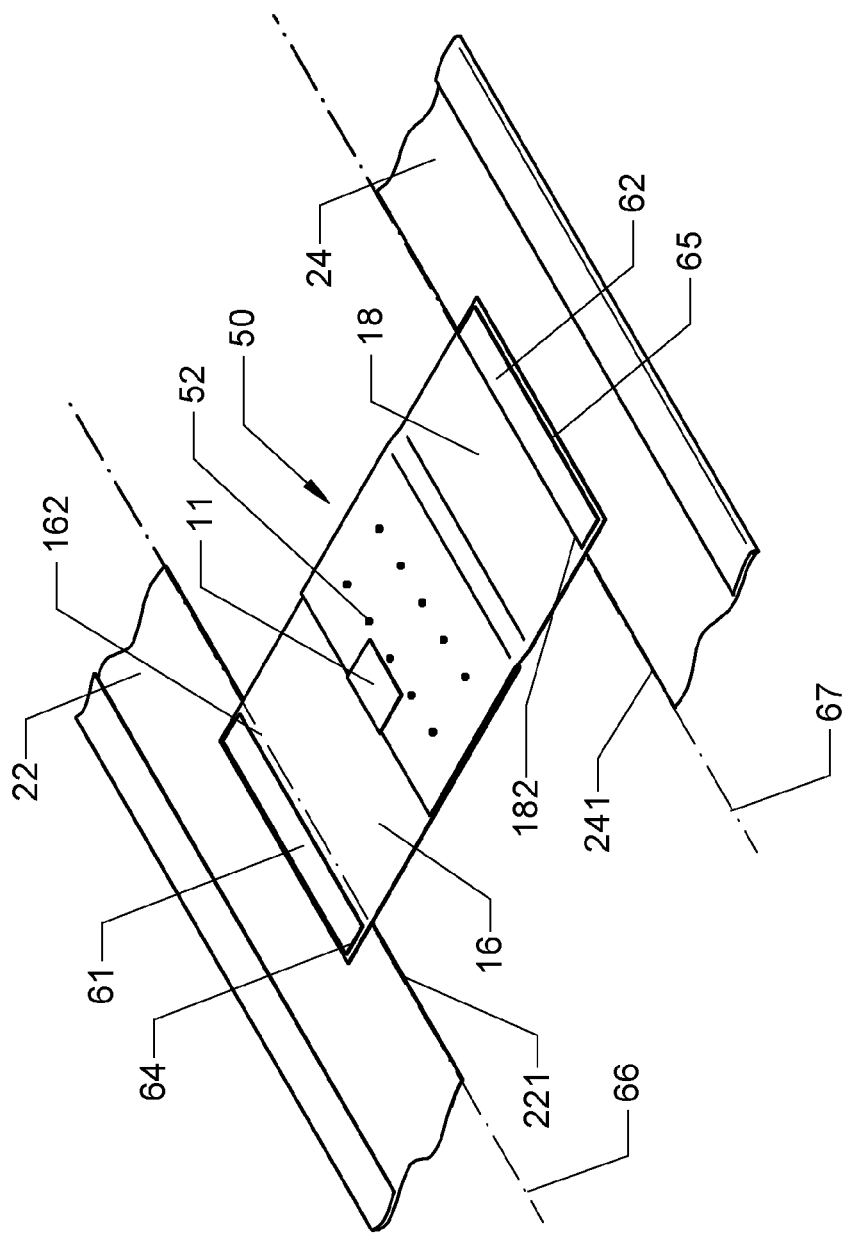
FIG. 4 is a perspective view of the semi-finished product according to the line III-III of FIG. 2.

In the preferred embodiment illustrated in FIGS. 3 and 4, the joint between the temporary laminate 50 and each side material 22, 24 can be produced by bringing into contact the second surface 505 of the temporary laminate 50 with the first surfaces 220 and 240 on each side material 22 and 24.

The joints 61 and 62 can be produced with any method known in the art, such as, for example: adhesives, ultrasonic welding or thermo-welding.

In the preferred embodiment shown in FIG. 2, the joints 61 and 62 can be welds produced by means of a thermo-welding unit 80 composed of a pair of counter-rotating rollers which can be heated.

There are various examples of equipment suitable for carrying out the welding of sheet materials available in the patent literature; purely by way of example see EP-B 0 295 957 "Dynamic mechanical bonding method and apparatus".

Once the semi-finished product formed by the temporary laminate 50 joined to the two side materials 22 and 24 is produced, as shown in FIGS. 3 and 4, it is sent to the folding apparatus 90, which envisages overturning the aforesaid side materials 22 and 24 in order to bring the second surface 225 of the first side tape 22 and the second surface 245 of the second side tape 24 in contact with the second surface 505 of the temporary laminate 50.

As shown in greater detail in FIG. 4, the overturning of the side sheets 22 and 24 is carried out by rotating them around two respective fold lines 66 and 67, parallel to the first end edges 221 and 241 of the aforesaid side materials 22 and 24. Each of these fold lines can be located in any point of the first end regions 222 and 242 or of the intermediate regions 224 and 244 of the side materials 22 and 24 or of the second non-overlapping regions of the temporary laminate 50.

In the preferred embodiment, as illustrated in FIGS. 3 and 4, the overturning of the panels is carried out along the fold lines 66 and 67, which typically coincide with the first end edges 221 and 241 of the side materials 22 and 24.

Examples of suitable equipment to carry out the described overturning operations are available in the patent literature, for example see U.S. Pat. No. 7,500,941 B2 "Folding system and process for a continuous moving web operation".

Immediately after having carried out the overturning of the side tapes 22 and 24, the construction of the upper sheet or topsheet 20 is completed by joining the central tape 21 to the two side sheets 22 and 24 by means of at least two joining lines 105, as shown in FIG. 5.

The joints 105 can be produced with any method known in the art. In the preferred embodiment, the aforesaid joints 105 are produced thanks to the adhesive tapes 101, spread on the sheet 21 by a device for glue application 100 known per se in the art.

Figure 6:
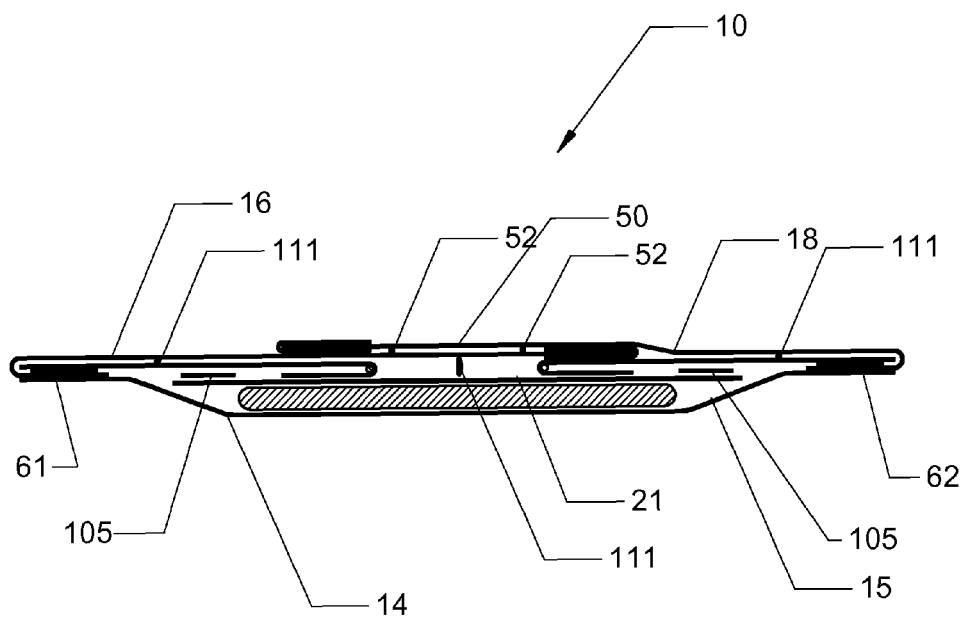
FIG. 6 is a cross-sectional view along the line VI-VI in FIG. 2.

In the preferred embodiment, illustrated in FIGS. 5 and 6, the central web 21 typically has a width that allows it to connect its end edges to the intermediate regions 224 and 244 of the side materials 22 and 24.

From FIG. 5 and FIG. 2, which illustrate the production method according to the preferred embodiment, it is possible to understand that the side panels 16 and 18 are always easily managed during the whole production process of the topsheet 20, thanks to the production of the temporary laminate 50 that has been inserted into the process to show, from the outset, the already-folded side panels 16 and 18 in their final required position; in this way, they are never moved or further processed.

In the preferred embodiment of FIG. 4, to further improve the stability of the side panels 16 and 18, with respect to the topsheet 20, it is possible to join, in a provisional manner, said temporary laminate 50 to at least one of the elements that make up the topsheet 20, or rather the central web 21 and/or the side materials 22 and 24. Aforesaid provisional union can be obtained by passing the semi-finished laminate of FIG. 5 through a welding unit 110, conceptually similar to the welding unit 70, able to produce the further provisional welds 111.

After having constructed the semi-finished product comprising the topsheet 20 with the side panels 16 and 18 fixed on it, the method of producing the sanitary article 10 is completed, joining the absorbent core 15 and the backsheet 14 to the topsheet 20, with means 114 known per se, as indicated schematically in FIG. 2. The chain of blanks of sanitary articles 10 can, at this point, be sent to the cutting unit 115, which envisages separating the individual absorbent products 10, which, subsequently, will be sent to further apparatuses capable of producing one or more folds parallel to the transverse axis Y-Y of the article 10 in order to confer the appropriate dimensions to it, in order to be able to package it in bundles that will be distributed on the market.

Of course, without prejudice to the principle of the invention, the details of construction and the embodiments may vary widely, even significantly, with respect to those illustrated here, purely by way of non-limiting example, without departing from the scope of the invention as defined by the attached claims that follow.

The invention claimed is:

1. A method for producing a sanitary article wearable in the manner of pants, comprising:
    a first side panel and a second side panel, each side panel having a first end region and a second end region;
    a first and a second side material intended to be fixed respectively to said first and second side panel, said first and second side material having respectively a first end edge and a first end region adjacent thereto, a second end region, an intermediate region between said first and second end region, a first surface and a second surface; and
    a central web intended to be fixed to said first and second side material, the method comprising the steps of:
        positioning said first side panel and said second side panel in a configuration of partial overlap, so that said first end region of said first side panel and said first end region of said second side panel are in contact with each other in an overlapping region, while said second end regions of said first and second side panel remain uncovered;
        provisionally joining said first end regions of said first and second side panel, so as to form a temporary laminate having a first surface and a second surface;
        joining said second end regions of the respective first and second side panel of said temporary laminate respectively to said first end regions of each side material;
        bringing into contact at least one portion of said second surface of each side material with said second surface of said temporary laminate; and
    joining said central web to said first and second side material.

2. A method according to claim 1, further comprising joining said second end regions of the respective first and second side panel of said temporary laminate to said first end regions of each side material by bringing into contact said second surface of said temporary laminate with said first surfaces of each side material.

3. A method according to claim 1, further comprising bringing into contact at least one portion of said second surface of each side material with said second surface of said temporary laminate by rotating each of said side materials about said respective first end edge.

4. A method according to claim 1, wherein said first end regions of said first and second side panel are joined together by provisional thermo-mechanical welding points.

5. A method according to claim 1, wherein said side panels are provided with coupling systems.

6. A method according to claim 1, wherein said second end regions of the respective first and second side panel of said temporary laminate are joined respectively to said first end regions of each side material by means of thermo-mechanical welding.

7. A method according to claim 1, wherein said second end regions of said side materials are provided with elastic elements.

8. A method according to claim 1, wherein said central web is joined to said intermediate regions of said first and second side material.

9. A method according to claim 1, comprising provisionally joining said temporary laminate with at least one of said central web and said side materials.

* * * * *